United States Patent
Doerr et al.

(10) Patent No.: US 8,611,979 B2
(45) Date of Patent: Dec. 17, 2013

(54) IMPLANTABLE ELECTRODE LEAD HAVING PREFORMATION AND STIFFENING STRUCTURE

(75) Inventors: Thomas Doerr, Berlin (DE); Gernot Kolberg, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/410,366

(22) Filed: Mar. 2, 2012

(65) Prior Publication Data

US 2012/0232370 A1    Sep. 13, 2012

Related U.S. Application Data

(60) Provisional application No. 61/450,144, filed on Mar. 8, 2011.

(51) Int. Cl.
  *A61B 5/04* (2006.01)
(52) U.S. Cl.
  USPC .......................................... 600/373; 607/116
(58) Field of Classification Search
  USPC .......................................................... 600/373
  See application file for complete search history.

(56) References Cited

U.S. PATENT DOCUMENTS

| | | | |
|---|---|---|---|
| 4,913,147 A * | 4/1990 | Fahlstrom et al. | 607/2 |
| 2007/0073130 A1* | 3/2007 | Finch et al. | 600/372 |

FOREIGN PATENT DOCUMENTS

| | | |
|---|---|---|
| EP | 0951920 | 10/1999 |
| WO | 2005046470 | 5/2005 |

OTHER PUBLICATIONS

European Search Report and Notes to the European Search Report on European Patent Application No. EP 12 15 7035, dated May 9, 2012 (5 pages).
Lendlein, Andreas and Langer, Robert, "Biodegradable, Elastic Shape-Memory Polymers for Potential Biomedical Applications", Science May 31, 2002: vol. 296 No. 5573 (pp. 1673-1676); DOI: 10.1126/science.1066102.

* cited by examiner

*Primary Examiner* — Christopher D Koharski
*Assistant Examiner* — Michael Carey
(74) *Attorney, Agent, or Firm* — Buchanan Ingersoll & Rooney PC

(57) ABSTRACT

An implantable electrode lead including an elongated electrode lead body having a proximal end and a distal end, at least one electrical supply lead which is enclosed in an electrically insulating material to electrically insulate the supply leads against the surroundings of the electrode lead, at least one electrically active surface which is disposed on the distal end, or in the vicinity thereof, and is connected to the at least one electrical supply lead, by way of which therapeutic signals can be output and/or diagnostic signals can be received, a plug disposed on the proximal end, which is electrically connected to the at least one electrical supply lead and can be connected to an electro-medical implant, and at least one preformed and/or stiffened section of the electrode lead body, which has an additional preformation and/or stiffening structure, by way of which the section is preformed and/or stiffened.

9 Claims, 6 Drawing Sheets

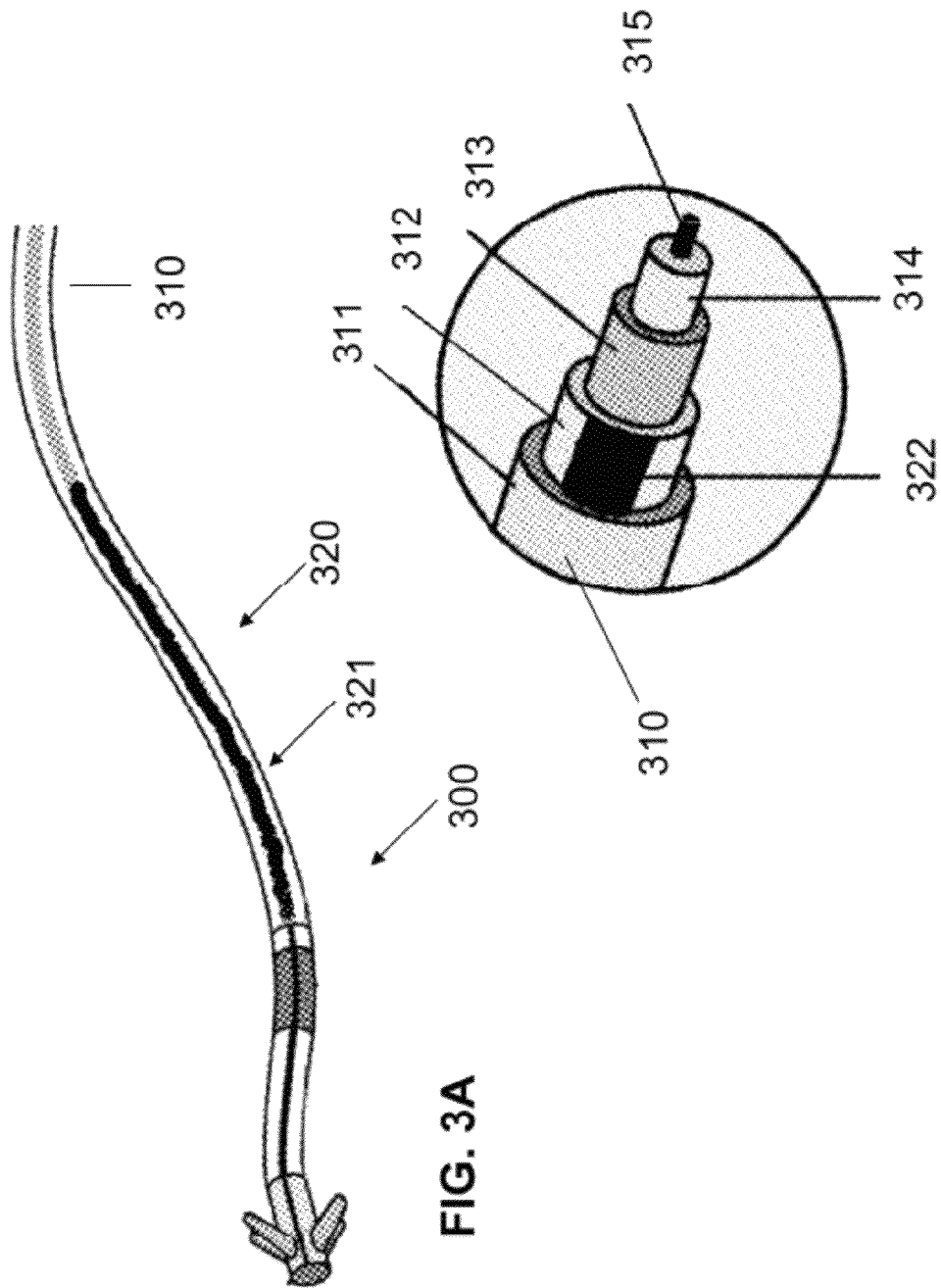

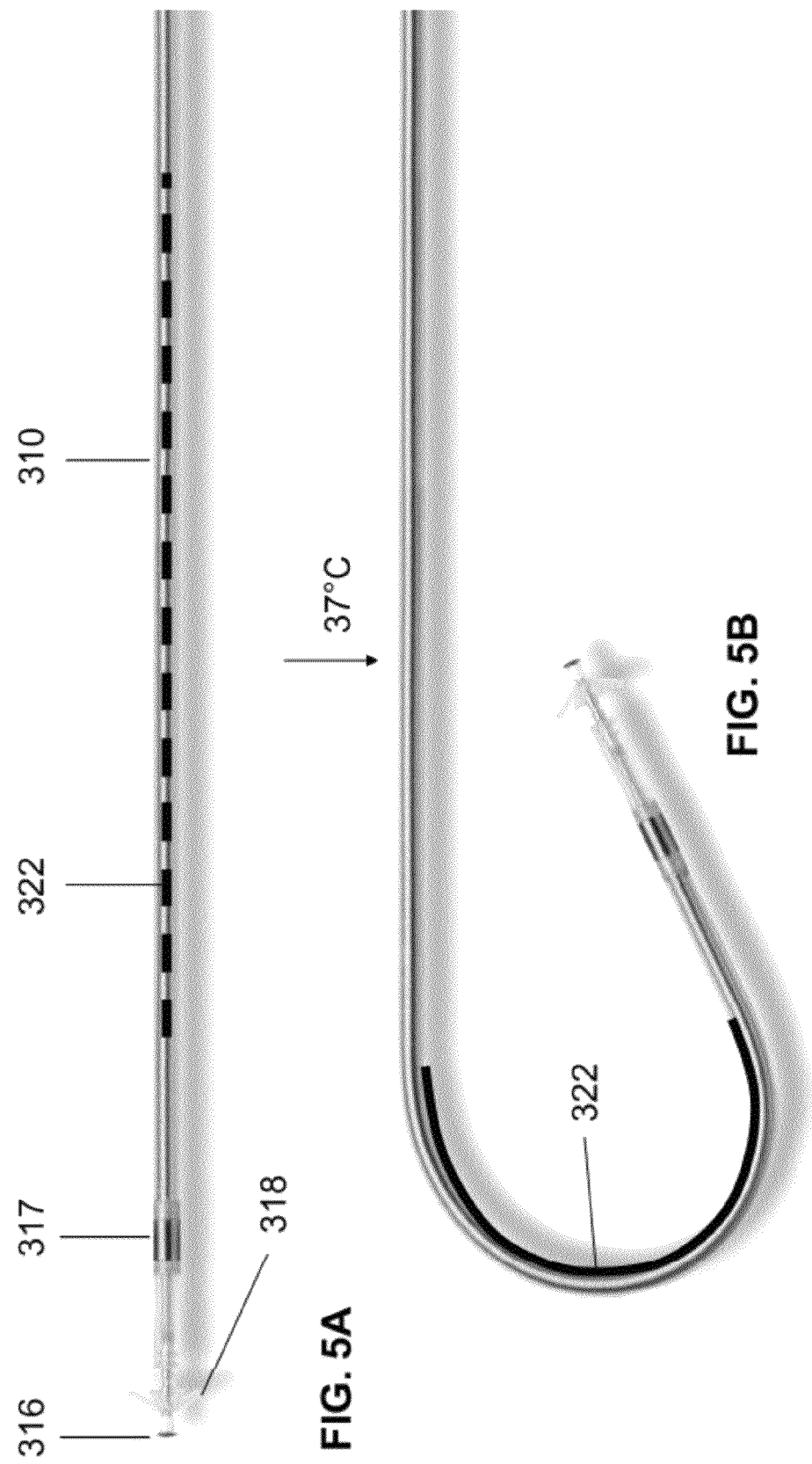

IMPLANTABLE ELECTRODE LEAD HAVING PREFORMATION AND STIFFENING STRUCTURE

CROSS-REFERENCE TO RELATED APPLICATIONS

This patent application claims the benefit of co-pending U.S. Provisional Patent Application No. 61/450,144, filed on Mar. 8, 2011, which is hereby incorporated by reference in its entirety.

TECHNICAL FIELD

The present inventive disclosure relates to an implantable electrode lead, such as, for example, electrode leads for electro-medical implants such as, for example, implantable cardiac pacemakers, cardioverters, defibrillators, nerve and brain stimulators, etc.

BACKGROUND

Such an electrode lead is comprised of an elongated body, the exterior of which is comprised of an insulating material, such as, for example, silicone or polyurethane. The body has a proximal end and a distal end. Situated on the proximal end is at least one plug which can be connected to a connector—which is usually a socket—in the connector housing of the implant. The plug can be standardized and can be designed according to one of the standards, namely, IS-1, IS-4, or DF-1. Each of the electrically active contacts of the plug is electrically connected to an electrical supply lead which, in turn, is usually electrically connected at the distal end thereof to an electrically active surface (also referred to as "electrode pole" or "electrode") which is located on the distal end or in the vicinity thereof. Each of the connecting lines is insulated. The electrically active surfaces are used to induce electrical therapy at the body part to be treated, such as, for example, in or on the heart, in or on the brain or on nerves, or to receive measurement signals for diagnostic purposes.

Electrode leads typically comprise at least one preformed and/or stiffened section of the electrode lead body. These preformed or stiffened sections are used for a plurality of purposes. For instance, the attachment properties of the electrode leads in the area to be treated can be improved substantially by the use of certain shapes, such as, for example, the shape of a "J", a helix, an "S", or an omega. In the case of electrode leads disposed in the coronary sinus, in particular, the morphology of the vascular wall limits the attachment method to that of securing a section of the electrode lead body in the vessel. The maximum lateral extension of the electrode lead in the preformed and/or stiffened section is predetermined by the diameter of the vessel intended for use as the application site, and is approximately 8 mm for a coronary sinus electrode lead.

Furthermore, preformations of an electrode lead section are known which are designed especially for coronary sinus electrode leads and electrode leads that are used, e.g., to stimulate the high septum, and which simplify the placement of the electrodes at certain points. For example, introducing a coronary sinus electrode lead into the coronary sinus is complicated in some ways and requires a great deal of practice.

A conventional electrode lead having the shape of a "J" is shown in FIG. 1. The design thereof is characterized by an electrode body 110 which is preformed in the distal region in the shape of a "J". The electrode comprises, on the proximal end thereof, a bipolar plug which is not depicted and can be designed according to, for example, the IS-1 standard, and comprises on the distal end thereof two electrode poles in the form of a head or tip electrode pole 120 and a ring electrode pole 130, and a mechanism for electrode attachment 140.

FIG. 2 shows the design of a known "J"-shaped electrode lead. It comprises an outer insulation 210 made of silicone or polyurethane ("PU"), for instance. An outer supply lead coil 220 for the connection of ring electrode 130, an inner insulation 230, and an inner supply lead coil 240 for the connection of tip electrode 120. Since the "J" shape in the electrode body is preformed, an inner lumen 250 for accommodating a guide wire is required for implantation, in order to straighten the electrode as it is being inserted into the atrium, and primarily to enable the attachment thereof.

The preformed and/or stiffened section of such a shaped electrode lead typically comprises an elastically preformed and/or stiffened preformation and stiffening structure designed as a core of tempered MP35N steel, for instance. The elasticity of the lead is generally predetermined by the suitable selection of the strength and material handling conditions of the steel core such that it can be straightened easily by the guide wire used for implantation. Such a core is known from European Patent No. EP 0 951 920.

This known preformation and/or stiffening of the electrode lead has a plurality of disadvantages. For example, the electrode leads according to the prior art require a guide wire for implantation in order to advance the preformed and/or stiffened section to the implantation site without damaging the vessel. For this purpose, an elongated guide wire is slid into the above-mentioned inner lumen, thereby straightening the preformed and/or stiffened section. However, this lumen substantially limits the design freedom, since electrode leads must be designed with substantially larger diameters. Such electrode leads can therefore not be used arbitrarily in any vessel.

Furthermore, it has proven disadvantageous that an electrode lead must have a certain minimum stiffness in the region of the preformed and/or stiffened sections to support the function thereof as an anchoring means or insertion aid. This relative stiffness causes permanent stressing of the tissue at the attachment site of the electrode lead in, for example, the endocardium or the coronary arteries. Greater stimulation thresholds are induced as a result, thereby possibly increasing the risk of dislocation or perforations of the surrounding cardiac muscle, which have been documented in a few cases.

A problem addressed by the present inventive disclosure is therefore that of eliminating the disadvantages of the electrode leads made known in the prior art, and of improving an electrode lead such that it can be inserted without the use of tools and can be implanted without harming the surrounding tissue.

The present inventive disclosure is directed toward overcoming one or more of the above-identified problems.

SUMMARY

At least one of the above-identified problems is solved by an electrode lead having the features of the independent claim(s). Advantageous developments of the inventive disclosure are the subject matter of the respective dependent claims.

The subject matter of this application is an implantable electrode lead comprising an elongated electrode lead body having a proximal end and a distal end, at least one electrical supply lead which is enclosed in an electrically insulating material to electrically insulate the supply leads against the surroundings of the electrode lead, at least one electrically active surface which is disposed on the distal end, or in the vicinity thereof, and is connected to the at least one electrical supply lead, by way of which therapeutic signals can be output or diagnostic signals or both can be received, at least one plug disposed on the proximal end, which is electrically connected to the at least one electrical supply lead and which can be connected to an electro-medical implant, and at least one preformed and/or stiffened section of the electrode lead body which has an additional preformation and/or stiffening structure, by way of which the section is preformed and/or stiffened.

The inventive subject matter is further characterized in that the additional preformation and stiffening structure comprises a material which is present in a first state, in which it is preformed and/or stiffened in order to preform and/or stiffen the preformation and stiffening structure, and which can be converted by the application of energy or degradation, or both, into a second state in which the shape or stiffness of the material, or both, and, therefore, the preformation and stiffening structure, is changed compared to the first state.

It is thereby ensured that the electrode lead has the minimum stiffness in the first state required to insert the electrode lead without the additional stiffening effect of a guide wire. At the same time it is ensured that, after a certain period of time when this minimum stiffness is no longer required, flexibility is increased such that the preformation and the stiffening nearly disappear, or at least are reduced. This deformation and/or stiffening is no longer required also because the relevant section has adhered to the tissue.

This embodiment of the preformed and/or stiffened section also makes it possible to completely eliminate a lumen for accommodating a guide wire or a mandrin, since this function is performed by the stiffening and preformation described initially.

It has been shown that the preformation and stiffening structure is ideally comprised of a shape memory polymer ("SMP") or a biodegradable polymer or a combination thereof. These two materials are excellently suited for implementing the required state change. Biodegradable polymers lose their stiffness by degradation. The following biodegradable polymers are particularly suited for this purpose: polydioxanone, polyglycolide, polycaprolactone, polylactic acid [poly-L-lactide, poly(D,L-lactide), and copolymers, and blends such as poly(L-lactide-co-glycolide), poly(D,L-lactide-co-glycolide), poly(L-lactide-co-D,L-lactide), poly(L-lactide-co-trimethylene carbonate), triblock copolymers], polysaccharides (chitosan, levan, hyaluronic acid, heparin, dextrane, cellulose, etc.), polyhydroxyvalerate, ethyl vinyl acetate, polyethylene oxide, polyphosphorylcholine, fibrin, albumin. However, others are contemplated.

SMPs lose their shape when heated above a transition temperature. The shape can be preformed during manufacture, and so the preformation sets in once the transition temperature has been exceeded. Examples of an SMP are poly(styrene-block-butadiene), polyetherketone (PEEK), poly(methyl methacrylate) (PMMA), and the like.

It is also possible to use butyl acrylate, the lateral chains of which are cross-linked by way of cinnamic acid groups under the effect of UV light, thereby producing a first geometry. These cross-linkings can be broken by the effect of light having a different wavelength applied by way of an appropriate optical fiber, thereby producing a second geometry.

Particularly advantageously these two properties are combined in that the aforementioned shape memory polymer is biodegradable. Examples of such materials are polyalkanoates, polyhydroxy acid compounds, polyphosphazenes, polyether esters, polyanhydrides, and the like.

The material of the preformation and stiffening structure is designed to assume at least two states. In the first state of the material, the preformation and stiffening structure is designed such that the preformed section of the electrode lead has the shape of a stiffened "J", a stiffened helix, a stiffened "S", a stiffened omega, or a stiffened elongated shape in general. It is thereby ensured that an electrode lead can be inserted and temporarily placed in the area to be treated until the electrode lead adheres, since the minimum stiffness required to ensure attachment is present. In the second state, the preformed section preferably must be substantially more flexible and lose the preformation and stiffening thereof nearly completely, or at least achieve a reduction in stiffness. The preformation of the preformation and stiffening structure in the second state of the material is therefore designed such that the preformed section of the electrode lead has a shapeless and elastic shape compared to the first state, and is elongated and flexible, in particular. As a result, the pressure on the surrounding tissue is minimized and the tissue is no longer disturbed by the preformed and stiffened electrode lead.

Particularly advantageously the electrode lead can assume a plurality of states in the preformed and/or stiffened section, which are adapted to the various phases of an implantation. For example, it is advantageous for the aforementioned section to be elongated and stiff in a first phase to thereby ensure the advancement thereof through the vessels to the desired point, for example, the heart, and for it to assume a preformed and stiffened state in a second phase, in which the electrode lead assumes a guidance—a curvature, for example, to facilitate insertion thereof into the coronary sinus—or a fixation which can be used to attach the electrode. The section can then lose the shape and become flexible once the electrode has fully adhered at the desired point. For this reason, the material of the preformation and/or stiffening structure can also be converted, e.g., by the application of energy or degradation, or both, to an intermediate state which is situated between the first state and the second state, in which it is preformed or stiffened, or both, in order to preform and/or stiffen the preformation and stiffening structure in a manner that differs from the first state. The preformation and stiffening structure preferably has a stiffened elongated shape in the first state of the material, for example, the shape of a stiffened "J", a stiffened helix, a stiffened "S", or a stiffened omega in the intermediate state of the material, and, in the second state of the material, a form that is shapeless and elastic compared to the first state or the intermediate state. In particular, it is elongated and flexible in the second state.

As described above, the material of the preformation and stiffening structure is comprised of a material that changes its state by the application of energy or degradation. The energy can be supplied in the form of body heat, in particular. In the normal state, the human body has a mean temperature of 36.5° Celsius. In addition to the change in shape, flexibility should also increase, and this occurs by way of the degradation of the material. The intermediate state of the material is induced by the application of energy, in particular heat in the range of 35° C. to 40° C., or degradation, or both, and the second state is induced only by degradation. The degradation can take place by rapid degradation occurring first, e.g., in the case of a multiple-layered design of the material, by way of an upper, rapidly degradable, outwardly lying, first polymer layer, and a second polymer which is enclosed entirely by the first polymer layer and degrades slowly. The second polymer can be a biodegradable SMP, for example.

The various aforementioned states occur at different time horizons to allot the necessary time to the various aforementioned phases. For example, the intermediate state of the material can set in within 0.5 to 10 minutes, and the second state can set in within 1 to 140 days.

DESCRIPTION OF THE DRAWINGS

The inventive subject matter will be described in greater detail in the following using preferred embodiments, with reference to the drawings and the reference characters noted therein. In the drawings:

FIGS. 3A and 3B show a preformed section of an electrode lead of the subject matter of the application;

FIGS. 5A and 5B show the arrangement, as an example, of the deformation and stiffening structure in the preformed section.

DETAILED DESCRIPTION

Figure 1:
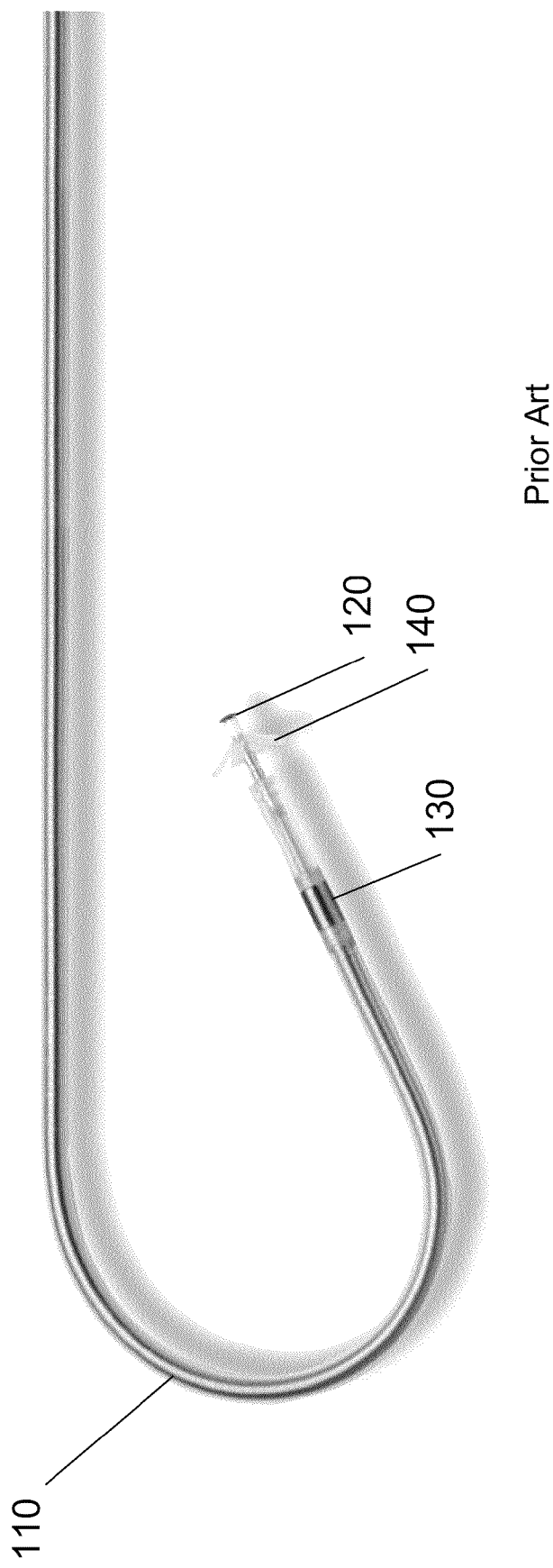
FIG. 1 shows an electrode lead comprising a section according to the prior art, which is preformed in the shape of a "J"
Figure 2:
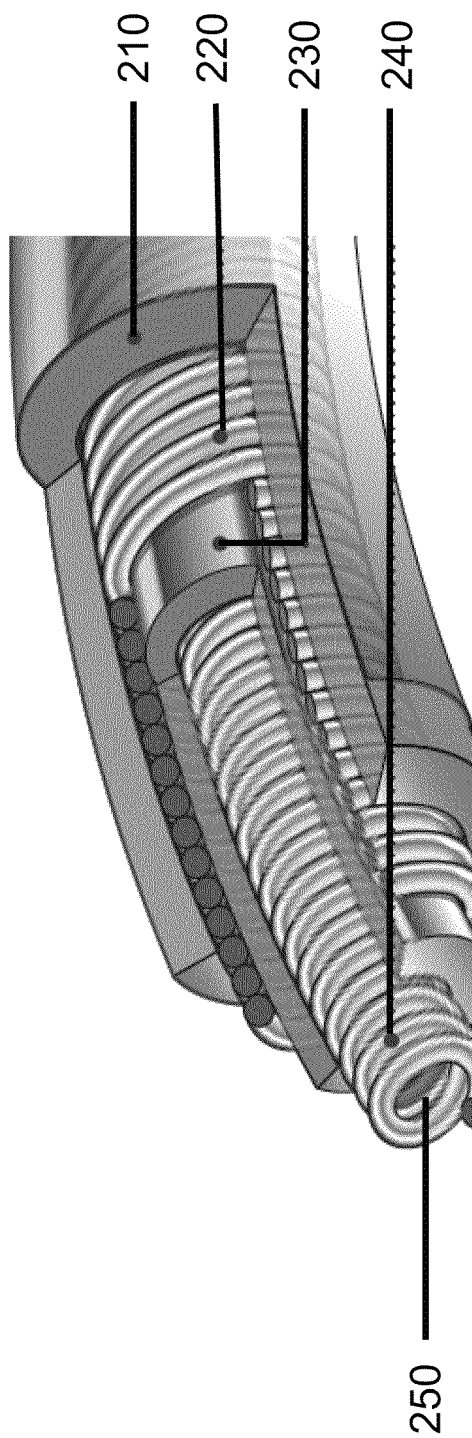
FIG. 2 shows the co-radial design of an electrode lead according to the prior art.

FIGS. 3A and 3B show a preformed and stiffened section of an electrode lead 300 of the subject matter of the application, which is designed as an SMP-J electrode lead. Electrode lead body 310 has a preformed section 320 which is provided with a preformation and stiffening structure 321. In one case, preformation and stiffening structure 321 can enclose the entire electrode lead body 310.

In another case, which is depicted in the enlarged partial sectional view in FIG. 3B, preformation and stiffening structure 321 can be a section 320 which is preformed and stiffened on one side and is preferably disposed in the distal region of electrode lead 300. It can be an SMP strip 322 which is initially deformed by way of temperature. In this case, electrode lead body 310 would be comprised of an external, biodegradable sliding and protective layer 311. Sliding and protective layer 311 protects SMP strip 322 which is disposed underneath thereof and is adhered to outer insulation 312 using a primer.

The inner design of electrode lead 300 inside external insulation 312 is similar to the design of a conventional electrode lead, with the difference that a guide wire lumen is not provided since the function of the guide wire is performed by the preformation and stiffening structure. It therefore comprises an external electrode helix 313 which is delineated from inner conductor 315 by inner insulation 314.

Figure 4B:
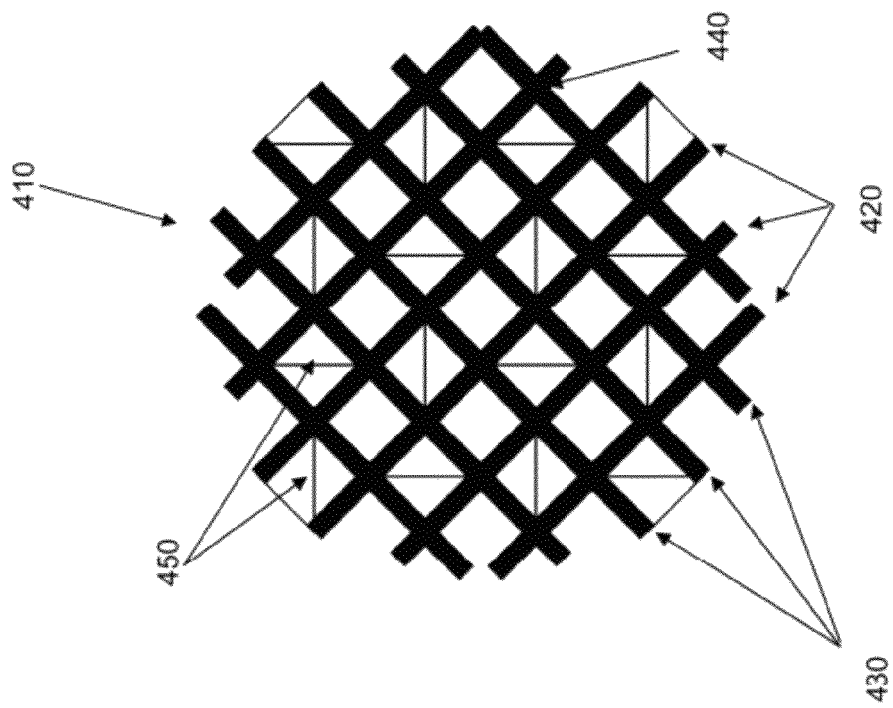
FIGS. 4A-4D show a design, as an example, of a latticed deformation and stiffening structure composed of shape memory polymer ("SMP")
Figure 4A:
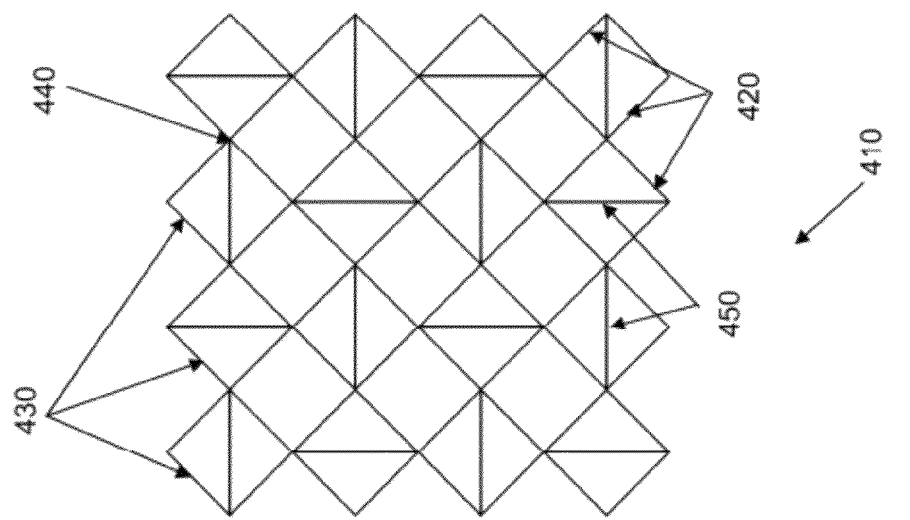
Figure 4D:
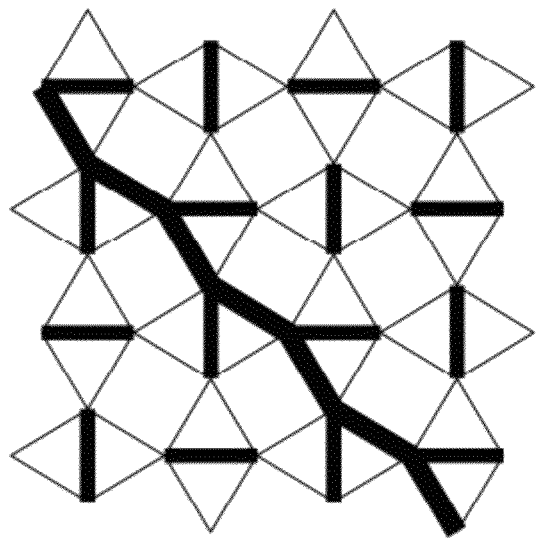
Figure 4C:
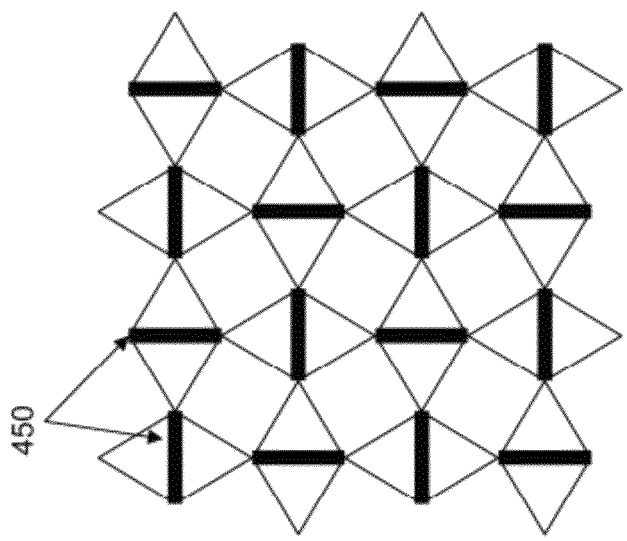

FIGS. 4A-4D show a design, as an example, of a latticed preformation and stiffening structure comprised of SMP, which is not applied as a strip on one side, as shown in FIG. 3B, but which can enclose the entire electrode lead body 310, as mentioned previously. A latticed structure 410 comprised of an SMP lattice is wound around the electrode 300. The structure generally comprises first struts 420 having a first winding direction, and second struts 430 having a second winding direction, wherein the first and the second winding direction are disposed in different directions around the electrode lead body 310, and so the first 420 and second 430 struts intersect at intersection points 440, preferably at nearly a right angle. However, other angles are contemplated. The first 420 and second 430 struts are elongated and have no angles. The first 420 and second 430 struts are interconnected at intersection points 440, e.g., being bonded or welded, and so the two struts 420 and 430 cannot be displaced relative to one another.

The electrode is stiffened in this manner. If the electrode is bent, first 420 and second 430 struts absorb tensile forces and increase the force required for bending. Intersection points 440 are also interconnected by way of lattice elements—which are transverse struts 450, in this example—in the manner shown. While first 420 and second 430 struts do not have a stored shape, transverse struts 450 are elongated. During implantation they are exposed to the patient's body heat and shorten after approximately 10 minutes (see e.g., FIGS. 4C and 4D).

The lattice structure is distorted as a result. The first 420 and second 430 struts are no longer straight and counteract the tensile forces in an elastic manner. This electrode lead is stiff in the preformed section during implantation and can be easily advanced and directed by the operator. Once the electrode lead has been fastened at the optimal point in the vessel, e.g., in the heart, it becomes soft and elastic. It therefore no longer offers mechanical resistance to the vascular system and is permanently stable.

According to a further embodiment, the shape memory effect can be utilized in another direction. While first struts 420 of a lattice structure lengthen in the aforementioned example, the lattice can also be designed such that second struts 430 lengthen instead of first struts 420, and thereby change the static properties of the lattice.

In a further embodiment, the shape memory effect is utilized can be both directions. For example, first struts 420 lengthen in certain sections of the deformation and stiffening structure, and second struts 430 do so in other sections. Individual struts 420 or 430 lengthen after they are inserted into the patient, while others shorten. The lattice structure is softened in this manner.

In a further embodiment—which is depicted with reference to an electrode lead for the high septum—the lattice structure of the preformation and stiffening structure is changed by the use of the shape memory effect and the degradation of the material, such that the electrode lead is stiffened in the region of the preformed section outside of the body and during advancement. Once inserted into the vascular system, the electrode lead body takes on different shapes in the various phases of implantation, the shapes being timed to coincide with implantation and the adhesion behavior.

At the beginning, the electrode lead is straight and very stiff in the region of the preformed section. The electrode lead body can therefore be inserted very easily into the insertion device and advanced.

After approximately 10 seconds, the lattice elements of the preformation and stiffening structure slowly shorten in the region of the preformed section, which is preferably disposed on the electrode tip, thereby disturbing the rigid lattice structure. The preformed section becomes softer in this region. The electrode lead can therefore be slid easily into, for example, the right ventricle of the heart without traumatizing the tissue.

After approximately 1 minute, the lattice elements of the deformation and stiffening structure have shortened on one side of the circumference to the extent that the electrode lead forms a large arch, for example. The electrode lead therefore moves automatically in the direction of the outflow passage of, for example, the right ventricle. After another minute has passed, a few elements on the preformed section shorten approximately on the opposite side of the arch and form a small arch facing the opposite direction. The electrode tip now points toward the patient's bundle of His and can be attached to the tissue using suitable holding mechanisms. Within a few weeks the preformation and stiffening structure—which is comprised of degradable shape memory material—typically degrades. The electrode lead has adhered by then. It now becomes soft and highly elastic for atraumatic, long-term operation.

FIGS. 5A and 5B show an assembly, as an example, of the deformation and stiffening structure in the preformed section. The shape-memory J electrode lead is shown in FIG. 5A as it appears upon delivery. Straight electrode lead body 310 has electrically conductive surfaces in the form of a tip electrode and a ring electrode 316 and 317, respectively, and a fastening mechanism 318. The preformation and stiffening structure, which is designed as shape-memory polymeric strips 322 having an elongated shape, are located in the region of the desired "J" deformation.

If this electrode lead is now implanted, shape memory strip 322 softens and shortens to the actual length thereof, and so the typical "J" shape forms within approximately 0.5 to 15 minutes. Of course, other time periods are contemplated.

In the embodiment of this electrode lead comprising a biodegradable protective layer and a biodegradable SMP strip, once the electrode lead has adhered, the mechanical stress in the region of the preformed "J" section can be markedly reduced, thereby relieving the cardiac tissue of stress in the region in which the electrode is fastened.

The embodiments of the present disclosure are not limited to the above-described examples and emphasized aspects but, rather, are possible in a large number of modifications that lie within the scope of handling by a person skilled in the art. For example, the time periods set forth are in are exemplary, and designs utilizing longer or shorter time periods may be implemented without departing from the spirit and scope of the present invention.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable electrode lead, comprising:
    an elongated electrode lead body having a proximal end and a distal end, and at least one electrical supply lead enclosed by an electrically insulating material to electrically insulate the at least one electrical supply lead against the surroundings of the electrode lead,
    at least one electrically active surface which is disposed on the distal end, or in the vicinity thereof, and is connected to the at least one electrical supply lead, by way of which therapeutic signals can be output or diagnostic signals can be received, or both,
    at least one plug disposed on the proximal end, which is electrically connected to the at least one electrical supply lead and which can be connected to an electromedical implant, and
    at least one preformed and/or stiffened section of the electrode lead body, which has an additional preformation and stiffening structure, by way of which the section is preformed and/or stiffened,
    wherein the additional preformation and stiffening structure comprises a material which is present in a first state, in which it is preformed and/or stiffened in order to preform and/or stiffen the preformation and stiffening structure, and which can be converted by degradation of the material into a second state in which the shape and/or stiffness of the material, or both and, therefore, the preformation and stiffening structure is changed compared to the first state.

2. The implantable electrode lead according to claim 1, wherein the preformation and stiffening structure in the first state of the material is designed such that the preformed section of the electrode lead has the shape of a stiffened "J", a stiffened helix, a stiffened "S", a stiffened omega, or a stiffened elongated shape.

3. The implantable electrode lead according to claim 1, wherein the preformation of the preformation and stiffening structure in the second state of the material is designed such that the preformed section of the electrode lead has a form that is shapeless and elastic compared to the first state, and, in particular, is elongated and flexible.

4. The implantable electrode lead according to claim 1, wherein the material of the preformation and/or stiffening structure can also be converted by degradation of the material to an intermediate state which is situated between the first state and the second state, in which the preformation and stiffening structure is preformed or stiffened or both, in order to preform and/or stiffen the preformation and stiffening structure in a manner that differs from the first state.

5. The implantable electrode lead according to claim 4, wherein the preformation and stiffening structure has a stiffened elongated shape in the first state of the material, the shape of a stiffened "J", a stiffened helix, a stiffened "S", or a stiffened omega in the intermediate state of the material, and, in the second state of the material, a form that is shapeless and elastic compared to the first state or the intermediate state, and, in particular being elongated and flexible.

6. The implantable electrode lead according to claim 4, wherein the intermediate state of the material sets in within approximately 0.5 to 10 minutes, and the second state of the material sets in within approximately 1 to 140 days.

7. The implantable electrode lead according to claim 1, wherein the material is a shape memory polymer, a biodegradable polymer or a combination thereof.

8. The implantable electrode lead according to claim 7, wherein the shape memory polymer is biodegradable.

9. The implantable electrode lead according to claim 1, wherein the material of the preformation and stiffening structure completely degrades after a period of time.

* * * * *